US012011097B2

(12) United States Patent
Yetukuri et al.

(10) Patent No.: US 12,011,097 B2
(45) Date of Patent: Jun. 18, 2024

(54) SEAT ASSEMBLY HAVING AN ADJUSTABLE HEAD RESTRAINT

(71) Applicant: LEAR CORPORATION, Southfield, MI (US)

(72) Inventors: Arjun Yetukuri, Rochester Hills, MI (US); Sajad Arabnejad, Ann Arbor, MI (US); Bradley C. Duncan, Harrison Township, MI (US); David A. Hein, Sterling Heights, MI (US); Mladen Humer, West Bloomfield, MI (US); Dean Rinke, Yale, MI (US); David Gallagher, Sterling Heights, MI (US)

(73) Assignee: LEAR CORPORATION, Southfield, MI (US)

( * ) Notice: Subject to any disclaimer, the term of this patent is extended or adjusted under 35 U.S.C. 154(b) by 847 days.

(21) Appl. No.: 17/036,615

(22) Filed: Sep. 29, 2020

(65) Prior Publication Data

US 2022/0095811 A1   Mar. 31, 2022

(51) Int. Cl.
*B60N 2/02* (2006.01)
*A47C 7/38* (2006.01)
(Continued)

(52) U.S. Cl.
CPC .............. *A47C 31/126* (2013.01); *A47C 7/38* (2013.01); *A61B 5/0205* (2013.01); *A61B 5/05* (2013.01); *A61B 5/24* (2021.01); *A61B 5/6893* (2013.01); *B60N 2/002* (2013.01); *B60N 2/874* (2018.02); *G01L 11/00* (2013.01); *G01S 13/04* (2013.01);

(Continued)

(58) Field of Classification Search
CPC ........ B60N 2/832; B60N 2/835; B60N 2/856; B60N 2/859; B60N 2/874; B60N 2/876
See application file for complete search history.

(56) References Cited

U.S. PATENT DOCUMENTS 7,066,545 B2   6/2006   Terada et al.
7,145,263 B2   12/2006  Nathan et al.
(Continued)

OTHER PUBLICATIONS

Daimler AG, "Seats: Mobile Office Centre of Wellbeing", Jun./Jul. 2013, https://media.daimler.com/marsMediaSite/en/instance/ko/Seats-Mobile-office-and-centre-of-wellbeing.xhtml?oid=9904017, 9 Pages.

(Continued)

*Primary Examiner* — Syed A Islam
(74) *Attorney, Agent, or Firm* — Brooks Kushman P.C.

(57) ABSTRACT

A seat assembly with an adjustable head restraint assembly capable of being adjusted based on an approximate stature or spatial location of an occupant in the seat assembly. A seat assembly may include a sensor in the seat to detect if an occupant is present. The sensor may include a plurality of bladders and pressure sensors, a radar system, or a neuro-monitoring sensor. The sensor may send a signal to a controller indicating the presence of an occupant. The controller may approximate the size and/or spatial location of the occupant and send an adjustment signal to the head restraint adjustment mechanism to adjust the head restraint assembly to an in-use position. The controller may determine that an occupant is not present and send an adjustment signal to the head restraint adjustment mechanism to adjust the head restraint assembly to a non-use position.

20 Claims, 6 Drawing Sheets

(51) Int. Cl.

| | |
|---|---|
| *A47C 31/12* | (2006.01) |
| *A61B 5/00* | (2006.01) |
| *A61B 5/0205* | (2006.01) |
| *A61B 5/05* | (2021.01) |
| *A61B 5/24* | (2021.01) |
| *B60N 2/00* | (2006.01) |
| *B60N 2/874* | (2018.01) |
| *G01L 11/00* | (2006.01) |
| *G01S 13/04* | (2006.01) |
| *G01S 13/06* | (2006.01) |
| *A61B 5/024* | (2006.01) |
| *A61B 5/08* | (2006.01) |

(52) U.S. Cl.
CPC ............... *G01S 13/06* (2013.01); *A61B 5/024* (2013.01); *A61B 5/0816* (2013.01)

(56) References Cited

U.S. PATENT DOCUMENTS

| | | | |
|---|---|---|---|
| 9,457,699 B2 | 10/2016 | Yetukuri et al. | |
| 10,358,070 B2 | 7/2019 | Diefenthaler et al. | |
| 11,433,792 B2* | 9/2022 | Mihm | B60R 22/48 |
| 2012/0235459 A1* | 9/2012 | Yetukuri | B60N 2/002 |
| | | | 297/391 |
| 2019/0049968 A1 | 2/2019 | Dean et al. | |
| 2022/0348123 A1* | 11/2022 | Johnson | B60N 2/01541 |

OTHER PUBLICATIONS

Toyota Motor Corporation, "Quick Guide", Copyright 2007, 74 Pages.

* cited by examiner

SEAT ASSEMBLY HAVING AN ADJUSTABLE HEAD RESTRAINT

TECHNICAL FIELD

The present disclosure generally relates to seat assemblies having a head restraint capable of adjustment.

BACKGROUND

Seats may be provided with head restraints that are capable of adjustment to various positions. An example of a seat having a head restraint that is capable of adjustment is disclosed in U.S. Pat. No. 10,358,070 by Lear Corporation, which issued on Jul. 23, 2019 to Diefenthaler, et al.

Vehicle occupants have a risk of injury due to whiplash if a head restraint assembly is not properly positioned for the occupant's stature. Vehicle occupants may not properly position a head restraint assembly associated with a seat assembly.

There is a desire for solutions/options that minimize or eliminate one or more challenges or shortcomings of current seat assemblies and/or components or portions of such seat assemblies. The foregoing discussion is intended only to illustrate examples of the present field and is not a disavowal of scope.

SUMMARY

The present disclosure teaches a seat assembly with an adjustable head restraint assembly capable of being adjusted based on an approximate stature or spatial location of an occupant in the seat assembly.

In embodiments, a seat assembly may include a sensor in the seat to detect if an occupant is present. The sensor may include a plurality of bladders and pressure sensors. The sensor may send a plurality of pressure readings to a controller indicating the presence of an occupant. The controller may approximate the size and/or spatial location of the occupant and send an adjustment signal to the head restraint adjustment assembly to adjust the head restraint assembly to an in-use position. The controller may determine that an occupant is not present and send an adjustment signal to the head restraint adjustment assembly to adjust the head restraint assembly to a non-use position.

With embodiments, the sensor may be a biometrics sensor capable of detecting and measuring biometrics of an occupant. The biometrics sensor may be a radar system transmitting microwaves of a known frequency and magnitude towards a seating surface. The radar system may receive a reflected energy wave from the occupant including the strength of the signal, frequency at arrival, and the angle of arrival. The radar system may send a reflected energy wave signal to the controller where it may be filtered. The controller may determine based on the filtered reflected energy wave signal that an occupant is present and may approximate the size and/or spatial location of the occupant. The controller may send an adjustment signal to the head restraint adjustment assembly to adjust the head restraint assembly to an in-use position. The controller may determine that an occupant is not present and send an adjustment signal to the head restraint adjustment assembly to adjust the head restraint assembly to a non-use position.

In embodiments, the biometric sensor may be a non-contact neuro-monitoring sensor capable of detecting and measuring neuroelectric activity from an occupant. The neuro-monitoring sensor may send a neuro-monitoring signal to the controller with information including the strength of the signal and the angle of arrival and the controller may filter it. The controller may determine based on the filtered neuro-monitoring signal that an item is present and whether that item is human. The controller may approximate the size and/or spatial location of the occupant if the item is human. The controller may send an adjustment signal to the head restraint adjustment assembly to adjust the head restraint assembly to an in-use position. The controller may determine that an occupant is not present and send an adjustment signal to the head restraint adjustment assembly to adjust the head restraint assembly to a non-use position.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Moreover, except where otherwise expressly indicated, all numerical quantities in this description and in the claims are to be understood as modified by the word "about" in describing the broader scope of this invention. The term "substantially," "generally," or "about" may be used herein and may modify a value or relative characteristic disclosed or claimed. In such instances, "substantially," "generally," or "about" may signify that the value or relative characteristic it modifies is within ±0%, 0.1%, 0.5%, 1%, 2%, 3%, 4%, 5% or 10% of the value or relative characteristic. Practice within the numerical limits stated is generally preferred. Also, unless expressly stated to the contrary, the description of a group or class of materials by suitable or preferred for a given purpose in connection with the invention implies that mixtures of any two or more members of the group or class may be equally suitable or preferred.

Figure 1:
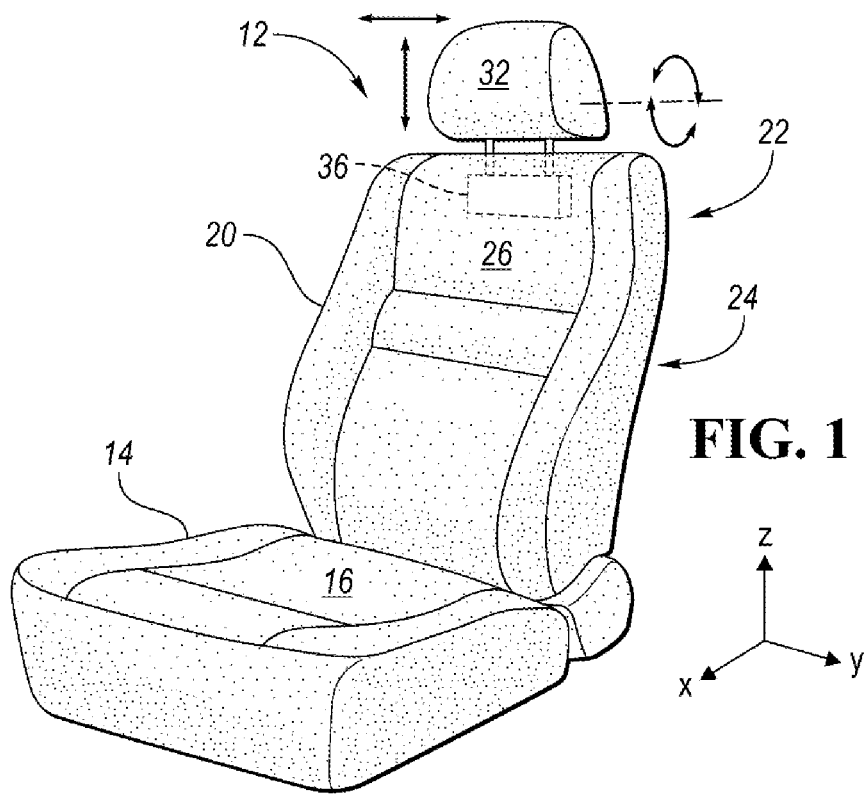
FIG. 1 is a perspective view of a seat assembly having an adjustable head restraint assembly.

Referring to FIG. 1, a seat assembly 12 is illustrated. The seat assembly 12 may, for example and without limitation, be used in conjunction with a passenger vehicle in any row (e.g., cars, vans, SUVs, trucks, buses, trains, boats, ships, planes, etc.), and may be utilized in any other situation or apparatus where seating is desired, such as recreational vehicles, commercial vehicles/equipment, agricultural vehicles/equipment, and/or roller coasters, among others. The seat assembly 12 has a seat cushion 14 and a seat back 20 mounted to the seat cushion. The seat back 20 has an upper portion 22 and a middle portion 24. The upper portion 22 and middle portion 24 have a front surface 26 that is capable of contacting an occupant 40. A head restraint 30 is attached to the seat back 20. The head restraint 30 has a front surface 32. The head restraint 30 may be capable of adjustment, such as height adjustment (translate along Z axis), fold forward or rearward (rotate around the Y axis), or depth adjustment (translate along X axis). A head restraint adjustment assembly 36 may be located in the head restraint 30 or seat back 20 and may be any motorized incremental adjustment assembly, such as a gear box, a rack and pinion, a ratchet, or the like.

Figure 9:
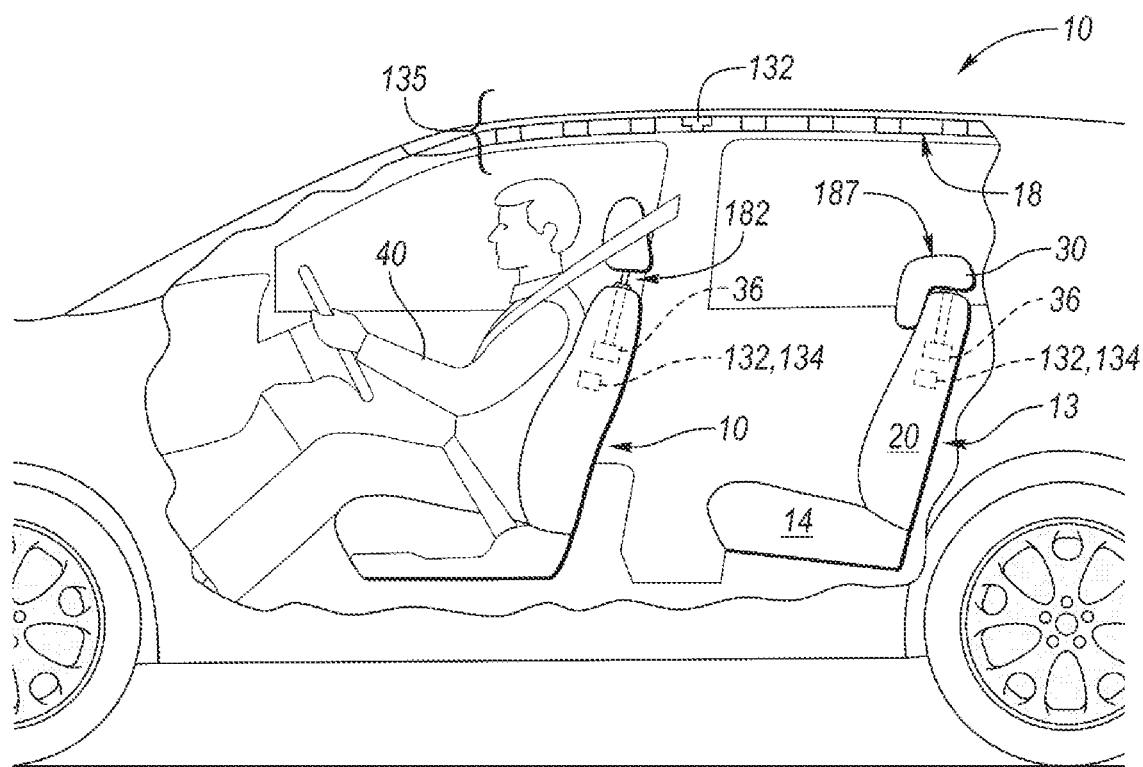
FIG. 9 is a side view of a passenger vehicle with seat assemblies having an adjustable head restraint assembly according to one embodiment of the present disclosure.

In embodiments, a sensor 100 may be attached to the seat assembly 12. The sensor 100 may be located outside or inside the seat back 20. The sensor 100 may be located in the upper portion 22 or middle portion 24 of the seat back 20 proximate a front surface of the seat back 26. The sensor 100 may be disposed on the front surface of the seat back 26. Additionally or alternatively, the sensor 100 may be attached to the head restraint 30. Similarly, the sensor 100 may be located inside the head restraint 30 proximate the front surface 32 of the head restraint 30 or disposed on the front surface 32 of the head restraint 30. Additionally or alternatively, the sensor 100 may be attached to the seat cushion 14. Similarly, the sensor 100 may be located inside the seat cushion 14 proximate a seating surface 16 or disposed on the seating surface 16. Additionally or alternatively, the sensor 100 may be attached to a headliner 18, structural pillars, instrument panels, consoles, or steering wheel of a passenger vehicle 10 (FIG. 9).

Figure 2:
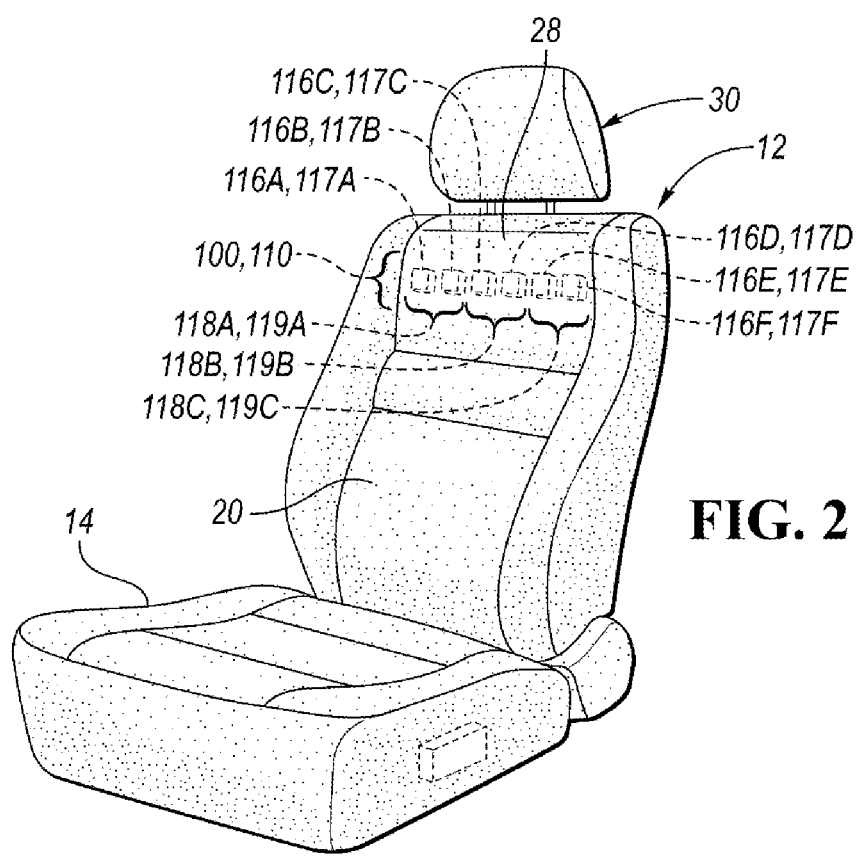
FIG. 2 is a perspective view of a seat assembly having an adjustable head restraint assembly according to one embodiment of the present disclosure.

With embodiments, and as shown in FIG. 2, the sensor 100 may be capable of detecting the presence or absence of an occupant 40 seated in a seat assembly 12. With embodiments, the sensor 100 may be a bladder system 110 capable of measuring, via a controller, changes in pressure. A bladder system 110 may have a compressor that provides a source of air. A plurality of valves 114 provide air to a plurality of bladders 116. A controller 104 controls the plurality of valves and regulates the air flow to and from the plurality of bladders 116. The plurality of bladders 116 may include a first bladder 116A, a second bladder 116B, a third bladder 116C, a fourth bladder 116D, a fifth bladder 116E, and a sixth bladder 116F in the upper portion 22 or middle portion 24 of the seat back 20 proximate to the front surface of the seat back 26. The plurality of bladders 116 may be arranged in a linear fashion substantially parallel to an edge 28 of the upper portion 22, however all configurations are contemplated including, but not limited to, arcuate or aciculate. The plurality of bladders 116 may include a plurality of paired bladders 118 such that the first bladder 116A and the second bladder 116B comprise a first pair 118A. Similarly, the third bladder 116C and fourth bladder 116D comprise a second pair 118B and the fifth bladder 116E and sixth bladder 116F comprise a third pair 118C.

In embodiments, each of the plurality of bladders 116 may include a pressure sensor 117A, 117B, 117C, 117D, 117E, 117F to detect air pressure in the respective bladder 116A, 116B, 116C, 116D, 116E, 116F. Similarly, each pair of the plurality of paired bladders 118 may include a pressure sensor 119A, 119B, 119C to detect air pressure in the respective pair of bladders 118A, 118B, 118C. Any pressure sensor is contemplated, such as a pneumatic pressure sensor at the outlet valve of each respective air bladder 116A, 116B, 116C, 116D, 116E, 116F or pair or pair of bladders 118A, 118B, 118C. Pressure can also be sensed by contact pressure sensors disposed in front of or behind some or all of the respective air bladders, including on a front or rear surface thereof. The contact pressure sensors may include pressure-sensing mats, such as those available by Tekscan®, Inc. of 307 West First Street. South Boston, Mass. 02127-1309, USA.

With embodiments, the controller 104 may receive a plurality of pressure readings 120, 122 from the plurality of pressure sensors 117, 119 signifying the presence or absence of an occupant 40. When an occupant 40 is present, the respective pressure sensors 117A, 117B, 117C, 117D, 117E, 117F, 119A, 119B, 119C may send pressure readings 120A, 120B, 120C, 120D, 120E, 120F, 122A, 122B, 122C for each bladder 116A, 116B, 116C, 116D, 116E, 116F or each pair of bladders 118A, 118B, 118C to the controller 104. Alternatively, pressure sensors 117A, 117B, 117C, 117D, 117E, 117F, 119A, 119B, 119C may report a change in pressure. The controller 104 may receive the plurality of pressure readings 120, 122 signifying an estimated stature or spatial location of an occupant 40 relative to the head restraint assembly 30 and send an adjustment signal 106 to the head restraint adjustment assembly 36 to adjust the head restraint assembly 30 to an in-use position or non-use position according to the present disclosure.

Figure 3A:
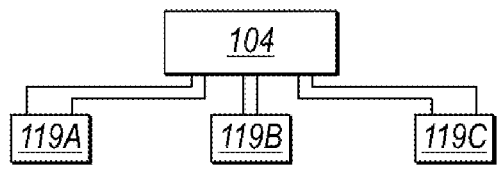
FIG. 3A depicts a sensor arrangement according to one embodiment of the present disclosure.
Figure 3B:
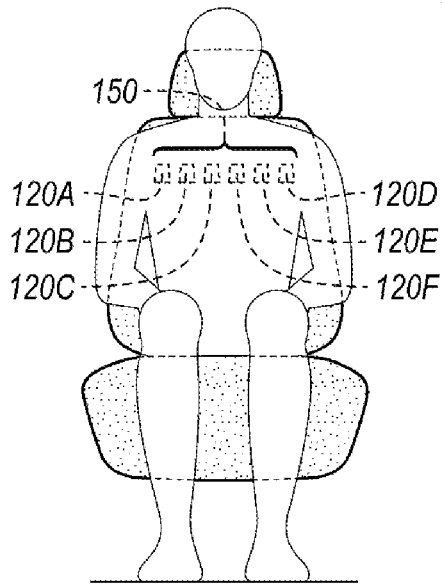
FIG. 3B is a front view of a seat assembly having an adjustable head restraint assembly according to one embodiment of the present disclosure.
Figure 3C:
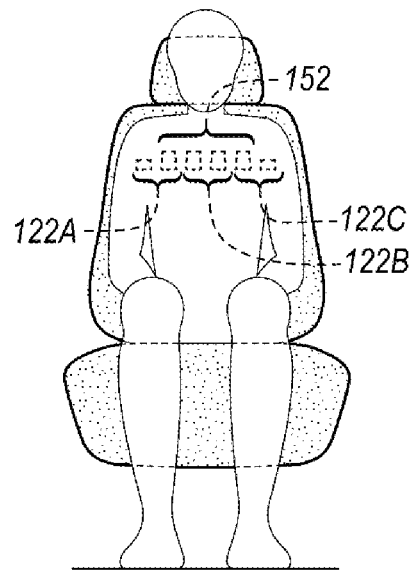
FIG. 3C is a front view of a seat assembly having an adjustable head restraint assembly according to one embodiment of the present disclosure.
Figure 3D:
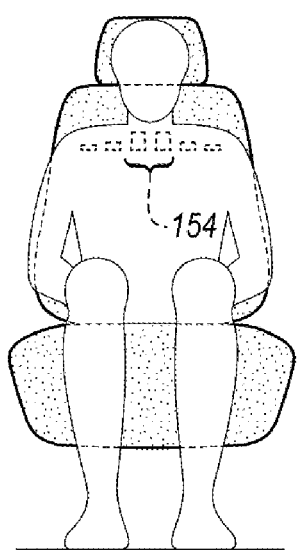
FIG. 3D is a front view of a seat assembly having an adjustable head restraint assembly according to one embodiment of the present disclosure.
Figure 3E:
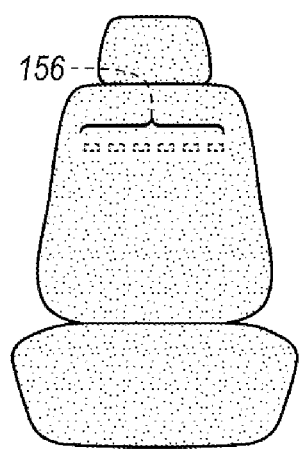
FIG. 3E is a front view of a seat assembly having an adjustable head restraint assembly according to one embodiment of the present disclosure.
Figure 3F:
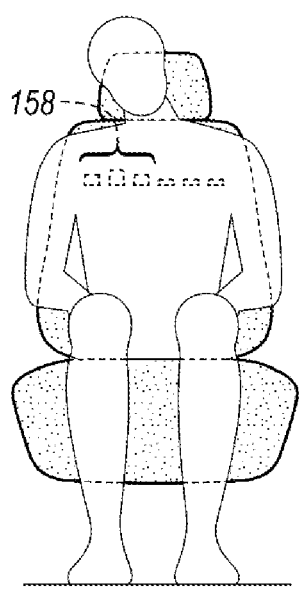
FIG. 3F is a front view of a seat assembly having an adjustable head restraint assembly according to one embodiment of the present disclosure.

A controller 104 may be located inside the seat back 20 or seat cushion 14 or outside the seat assembly 12 such as under the seat cushion 14. The controller 104 may compare the pressure readings 120A, 120B, 120C, 120D, 120E, 120F, 122A, 122B, 122C against a threshold value or nominal value to determine if an occupant 40 is present or absent. Pressure readings from sensors 117A, 117B, 117C, 117D, 117E, 117F, 119A, 119B, 119C may signify the approximate stature or spatial location of the occupant 40 relative to the head restraint assembly 30. In scenario A 150, and as shown in FIG. 3B, if each bladder 116A, 116B, 116C, 116D, 116E, 116F of the plurality of bladders 116 register a change in pressure or the controller 104 registers a pressure reading 120A, 120B, 120C, 120D, 120E, 120F above a threshold or nominal pressure, then that may be an indication that the occupant 40 is above a specific height. In scenario B 152, and as shown in FIG. 3C, if the second bladder 116B, the third bladder 116C, the fourth bladder 116D, and the fifth bladder 116E register a change in pressure or the controller 104 registers a pressure reading 120B, 120C, 120D, 120E above a threshold or nominal pressure, then that may be an indication that the height of occupant 40 is within a specified range. In scenario C 154, and as shown in FIG. 3D, if the third bladder 116C and the fourth bladder 116D, or the second pair of bladders 118B, register a change in pressure or the controller 104 registers a pressure reading 120C, 120D, 122B above a threshold or nominal pressure, then the head or neck of the occupant 40 is located at the height of the plurality of bladders 116. In scenario D 156, and as shown in FIG. 3E, if none of the respective bladders 116A, 116B, 116C, 116D, 116E, 116F register a change in pressure or the controller 104 does not register a pressure reading 120A, 120B, 120C, 120D, 120E, 120F above a threshold or nominal pressure, then the occupant 40 is absent. In scenario E 158, and as shown in FIG. 3F, if the first bladder 116A, the second bladder 116B, and the third bladder 116C register a change in pressure or the controller 104 registers a pressure reading 120A, 120B, 120C above a threshold or nominal pressure, then the head 42 or neck of the occupant 40 is offset. Alternatively, any subset of the plurality of bladders 116 (e.g. second bladder 116B, third bladder 116C, and fourth bladder 116D; or fourth bladder 116D and fifth bladder 116E) or any pair of the plurality of paired bladders 118 may register a plurality of pressure readings 120, 122 and signify the presence of an occupant 40.

Figure 4:
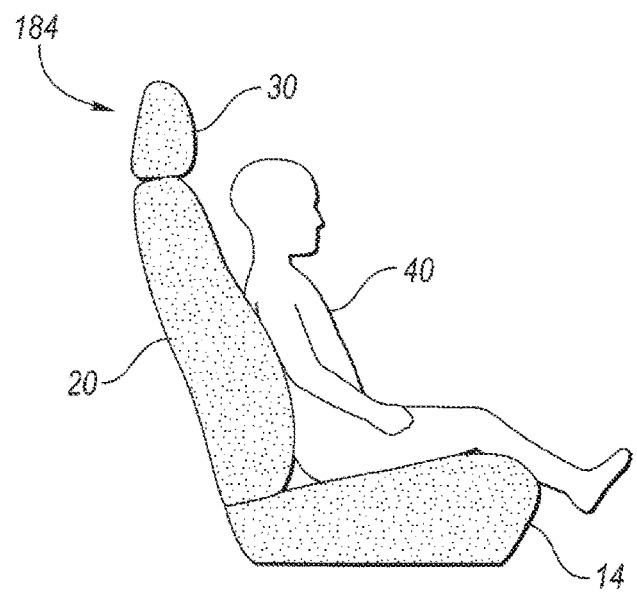
FIG. 4 is a side view of a seat assembly having an adjustable head restraint assembly according to one embodiment of the present disclosure.
Figures 5, 6:
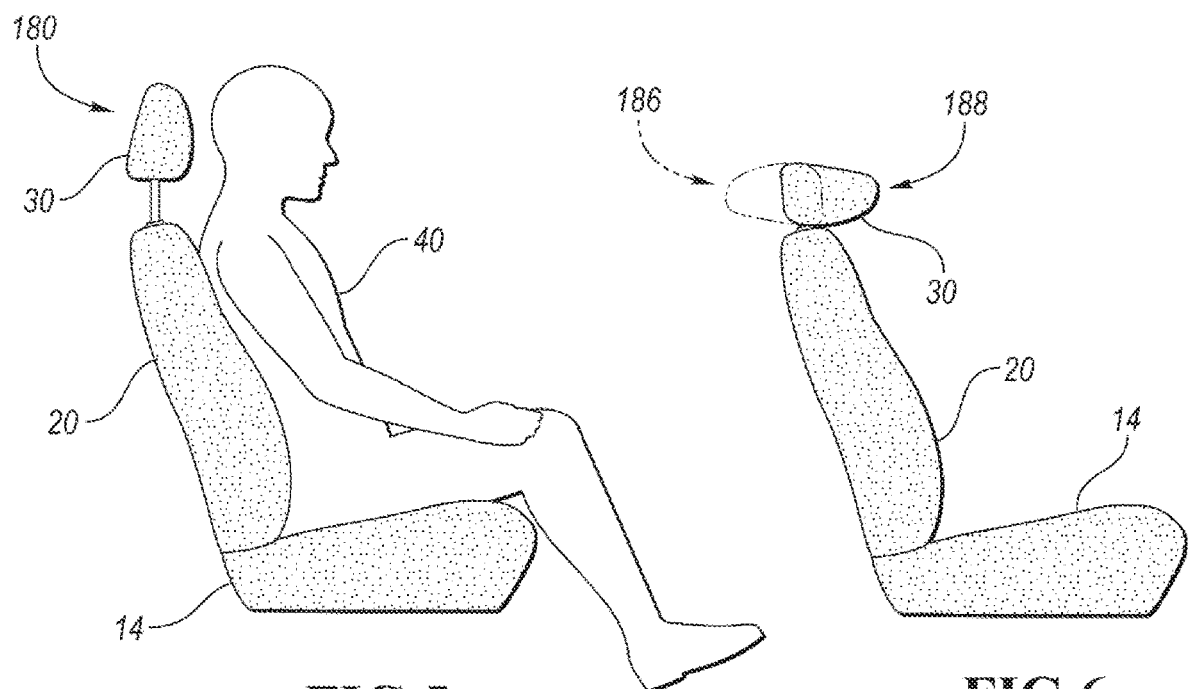
FIG. 5 is a side view of a seat assembly having an adjustable head restraint assembly according to one embodiment of the present disclosure.
FIG. 6 is a side view of a seat assembly having an adjustable head restraint assembly according to one embodiment of the present disclosure.
Figure 7:
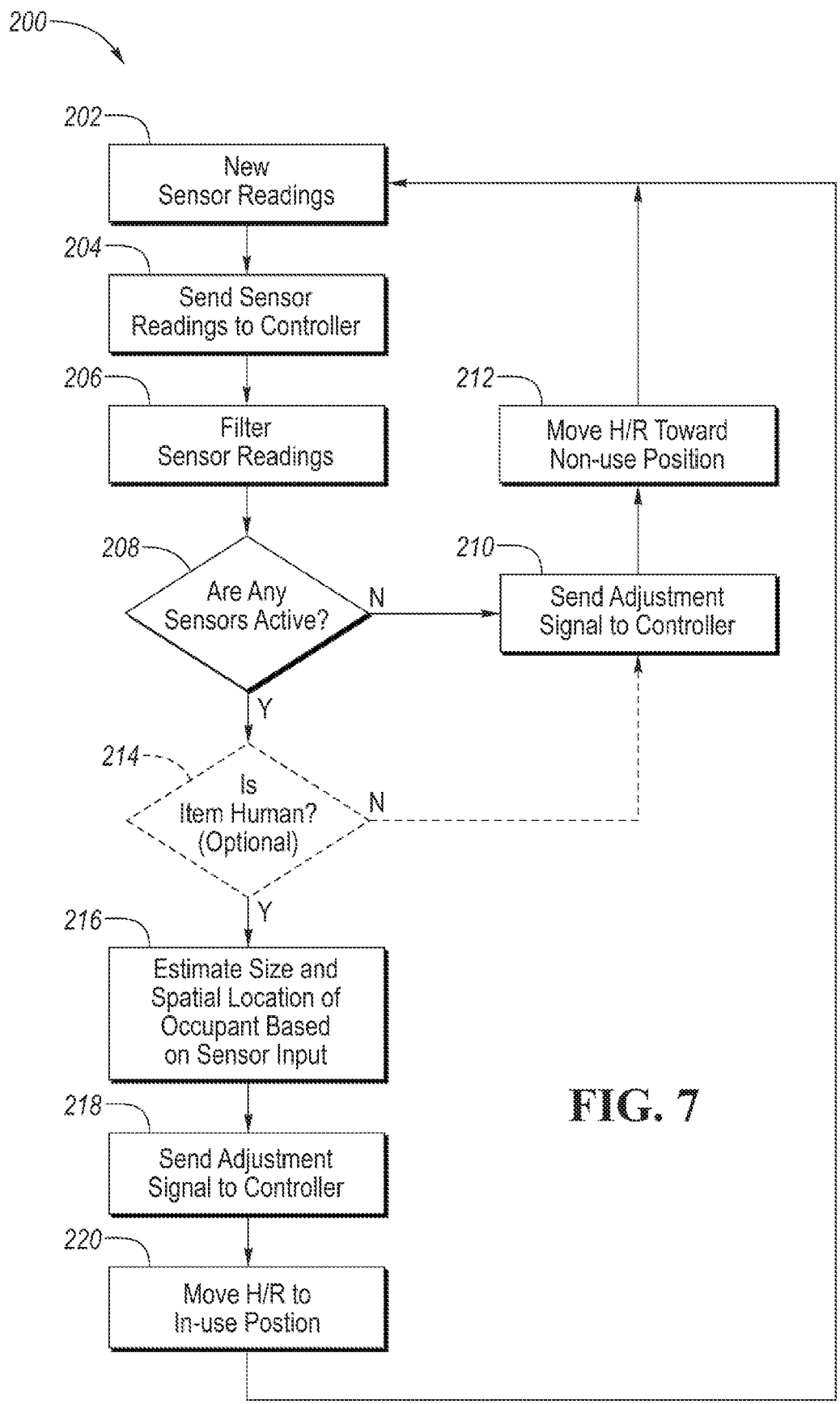
FIG. 7 is a flow diagram generally illustrating an embodiment according to present disclosure.

A plurality of bladders 116 and a plurality of pressure sensors 117 or a plurality of paired bladders 118 and a plurality of pressure sensors for paired bladders 119 may acquire pressure readings 120, 122 at step 202 in FIG. 7. At step 204, pressure readings 120, 122 are sent to the controller 104. At step 206, the controller 104 may filter pressure readings 120,122 to determine which bladders 116A, 116B, 116C, 116D, 116E, 116F or pair of bladders 118A, 118B, 118C are active. As described above, the controller 104 may compare the pressure readings 120, 122 to a threshold or nominal pressure. Alternatively, the pressure sensors 117A, 117B, 117C, 117D, 117E, 117F, 119A, 119B, 119C may report a change in pressure. At step 208, the controller 104 may determine whether any of the bladders 116, 118 are active. If no bladders 116A, 116B, 116C, 116D, 116E, 116F or pair of bladders 118A, 118B, 118C are active, determined at step 210, the head restraint assembly 30 via the head restraint adjustment assembly 36 may move towards a full-down position 184 as shown in FIG. 4 or a stowed position 186, 188 as shown in FIG. 6 at step 212. The process may start all over again at step 202 such that the plurality of bladders 116 and the plurality of pressure sensors 117 or the plurality of paired bladders 118 and the plurality of pressure sensors for paired bladders 119 may send pressure readings 120, 122 to the controller 104. If the controller 104 determines that bladders 116A, 116B, 116C, 116D, 116E, 116F or a pair of bladders 118A, 118B, 118C are active, then at step 208, the controller 104 may identify which bladders are active or which pressure sensors 117A, 117B, 117C, 117D, 117E, 117F, 119A, 119B, 119C are registering a pressure change. At step 216, the controller 104 may approximate the stature or spatial location of the occupant 40 based on which bladders 116, 118 are active. At step 208, the controller 104 may compare the active bladders 116, 118 to known scenarios, such as scenarios 150, 152, 154, 156, 158 outlined above. If the active bladders 116, 118 match scenario A 150, B 152, C 154, E 158 then the controller 104 may send an adjustment signal 106 at step 218 to the head restraint adjustment assembly 36 to move the head restraint assembly 30 at step 220 towards an in-use position. If the active bladders 116, 118 match scenario A 150 or B 152, then the controller 104 may send an adjustment signal 106 at step 218 to the head restraint adjustment assembly 36 to move the head restraint assembly 30 at step 220 towards a full up position as shown in FIG. 5. If the active bladders 116, 118 match scenario C 154 or E 158, then the controller 104 may send an adjustment signal 106 at step 218 to the head restraint adjustment assembly 36 to move the head restraint assembly 30 towards a mid-travel position 182. The controller 104 may return to step 202 and repeat the process during regular intervals or when the pressure sensors 117A, 117B, 117C, 117D, 117E, 117F, 119A, 119B, 119C detect a change.

In an embodiment, the sensor 100 may detect and measure, via a controller 104, biometrics of an occupant 40, such as heart rate, heart rate variability, breathing rate, breathing rate variability, or the like. The sensor 100 may be a radar system 130, such as continuous wave, sinusoidal frequency-modulated continuous wave radar (FMCW), unmodulated continuous wave radar (CW), or pulse radar, to detect the presence or absence of an occupant 40. The radar system 130 may have a transmitter 132 and a receiver 134. The transmitter 132 and receiver 134 may have at least one antenna, but multiple antennas are also contemplated. Additionally or alternatively, the radar system 130 may have a plurality of transmitters and receivers 135.

Figure 8A:
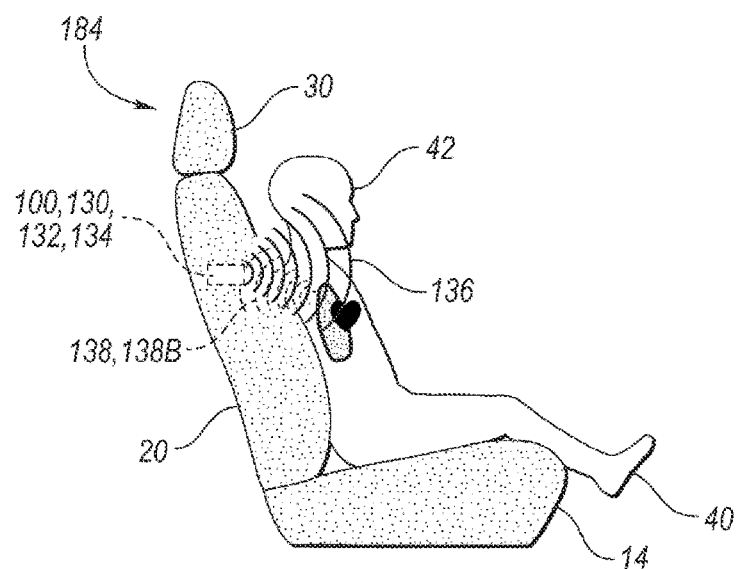
FIG. 8A is a side view of a seat assembly having an adjustable head restraint assembly according to one embodiment of the present disclosure.
Figure 8B:
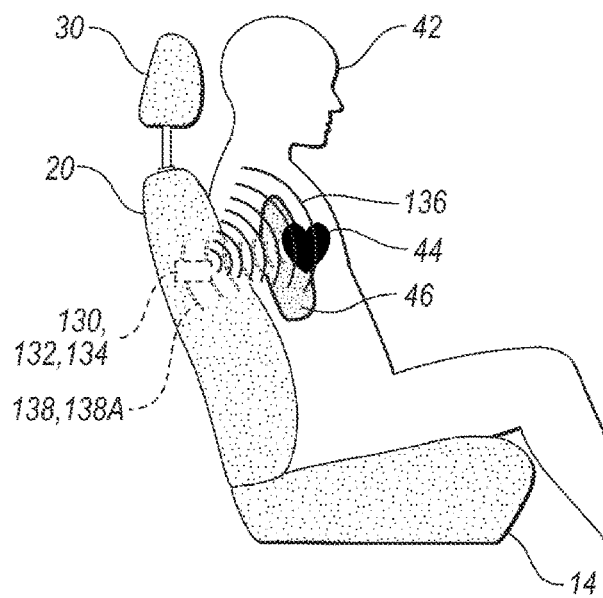
FIG. 8B is a side view of a seat assembly having an adjustable head restraint assembly according to one embodiment of the present disclosure.
Figure 8C:
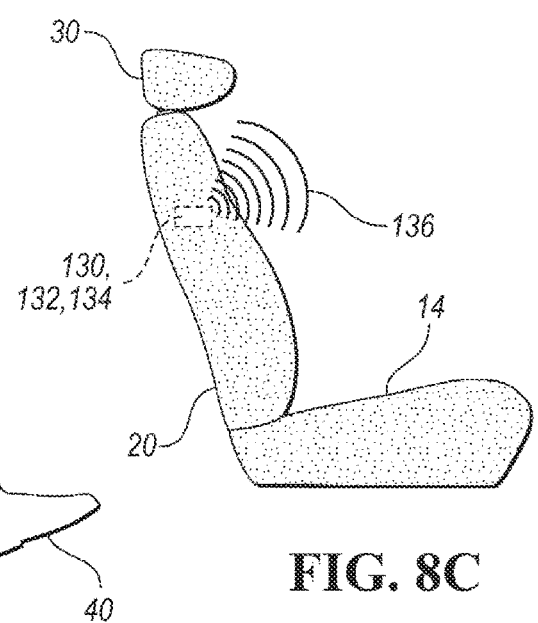
FIG. 8C is a side view of a seat assembly having an adjustable head restraint assembly according to one embodiment of the present disclosure.

Referring to FIGS. 8A-8C, the transmitter 132 may transmit a continuous wave of radio energy of a known frequency 136 in a direction of the occupant 40 and the receiver 134 may receive the reflected energy wave 138. If an occupant is present, the reflected energy wave 138 may include components 138A, 138B reflected off of a cardiac or respiratory activity of the occupant 40. The receiver 134 may transmit the reflected energy wave 138, 138A, 138B to a controller 104 to determine a spatial location of the occupant 40. For example and without limitation, the transmitter 132 may emit a continuous wave of radio energy 136 towards a seating surface 16. The occupant 40 may be present or absent. If the occupant is present, a continuous wave of radio energy 136 may reflect off of a cardiac or respiratory activity of the occupant 40 and the receiver 134 may receive the reflected energy wave 138, 138A, 138B. The receiver 134 may send a reflected energy wave signal 140 to the controller 104 with time and angle of arrival information of the reflected energy wave 138, 138A, 138B. The controller 104 may approximate the spatial location of the occupant 40 by filtering the reflected energy wave 138 to remove the continuous wave of radio energy 136 and use the filtered reflected energy wave 144, 144A, 144B to triangulate the heart 44 or lungs 46 of the occupant 40. The controller 104 may send an adjustment signal 106 to the head restraint adjustment assembly 36 to adjust the head restraint assembly 30 to an in-use position (i.e. full-up position 180, mid travel position 182, or full down 184 position). The adjustment signal 106 may be based a predetermined distance between the triangulated location of the heart 44 or lungs 46 and the head 42. If the occupant is absent, the continuous wave of radio energy 136 may reflect off the interior of the vehicle and the receiver 134 may receive a reflected energy wave 138 with a frequency that is substantially similar to the continuous wave of radio energy 136. The receiver 134 may send a reflected energy wave signal 140 to the controller 104 with time and angle of arrival information. The controller 104 may filter the reflected energy wave 138 to remove the continuous wave of radio energy 136. This may result in a signal 144 with no time or angle of arrival information for the controller 104 to triangulate a heart 44 or lungs 46 of the occupant 40. The controller 104, receiving no time or angle of arrival information for an occupant 40, may send an adjustment signal 106 to the head restraint adjustment assembly 36 to adjust the head restraint assembly 30 to a non-use position (i.e. full down position 184 or stowed position 186, 187, 188).

The reflected energy wave 138 may have a strength characteristic 138C indicative of the location of an occupant 40 relative to the seat assembly 12. For example and without limitation, an occupant 40 may be absent from a second row seat assembly 13 (i.e the second row seat assembly 13 is unoccupied) but an occupant 40 may be seated in a first row seat assembly 12 (as shown in FIG. 9). The reflected energy wave 138 may be weaker (i.e. have a greater rate of decay) because it is being reflected from an occupant 40 who is not in the second row seat assembly 13 (i.e. farther from the receiver 134 than expected). The receiver 134 may send a reflected energy wave signal 140 to the controller 104 with time and angle of arrival information. The controller 104 may approximate the spatial location of the occupant 40 by filtering the reflected energy wave 138 to remove the continuous wave of radio energy 136 and use the filtered reflected energy wave 144, 144A, 144B to triangulate the heart 44 or lungs 46 of the occupant 40. The weaker reflected energy wave 138 may indicate that an occupant 40 is not in the second row seat assembly 13. The controller 104, receiving a weaker reflected energy wave 138, may send an adjustment signal 106 to the head restraint adjustment assembly 36 to adjust the head restraint assembly 30 to a non-use position (i.e. full down position 184 or stowed position 186, 187, 188).

In embodiments, the reflected energy wave 138 may have a strength characteristic 138C indicative of the location of an occupant 40 relative to the seat assembly 12. For example and without limitation, if the heart 44 or the lungs of the occupant 40 are located directly in front of the receiver 134 in a XY plane, then the strength characteristic 144C of a filtered reflected energy 144 will be strong (e.g. a smaller rate of decay). If the heart 44 or the lungs of the occupant 40 are located above or below the receiver 134 in a YZ plane or located to the right or left of the receiver 134 in a XY plane, then the strength characteristic 144C of a filtered reflected energy 144 will be weak (e.g. have a greater rate of decay).

With embodiments, the receiver 134 may have multiple antennas. The plurality of antennas may increase the accuracy of the approximate spatial location of the occupant 40 by receiving reflected energy waves 138, 138A, 138B at each respective antenna. Each of the antennas may receive a reflected energy wave 138. The time the reflected energy wave 138 may take to reach the respective antenna and the angle of arrival may be indicative of the location of the occupant 40 relative to the respective antenna. The receiver 134 may send a reflected energy wave signal 140 to the controller 104 with time and angle information for each respective antenna. The controller 104 may calculate a more accurate spatial location of the occupant using a plurality of receivers 135 where each receiver, having multiple antennas, provides a reflected energy wave signal 140 with time and angle of arrival information for each respective antenna.

In embodiments, as shown in FIG. 9, the radar system 130 may encompass the entire passenger cabin of the vehicle 10 and be used to monitor and control multiple seat assemblies 12. A plurality of receivers 135 may be attached to a headliner 18 of a vehicle 10. The transmitter 132 may be centrally located for all occupants 40, or transmitters 132 may be located on each seat assembly 12 as described above (i.e. inside a seat back or seat cushion, on a seating surface, or on a front surface of the seat back). Each of the plurality of receivers 135 may receive a reflected energy wave 138, 138A, 138B. The time the reflected energy wave 138, 138A, 138B. may take to reach the respective receiver and the angle of arrival may be indicative of the location of the occupant 40 relative to the respective receiver. The receiver 134 may send a reflected energy wave signal 142 to the controller 104 with time and angle information for each respective receiver. The controller 104 may calculate a spatial location of each occupant 40 using a plurality of receivers 135 and send an adjustment signal 106 to the head restraint adjustment assembly 36 to adjust the head restraint assembly 30 to a non-use position (i.e. full down position 184 or stowed position 186, 187, 188).

With embodiments, the sensor 100 may be a non-contact neuro-monitoring sensor 162 (e.g. field sensing), to detect and measure neuroelectric activity of an occupant 40. The sensor 100 may be located inside the head restraint assembly 30 proximate a front surface 32 of the head restraint 30 or disposed on the front surface 32 of the head restraint 30. The neuro-monitoring sensor 162 may have at least one antenna, but multiple antennas are also contemplated. The neuro-monitoring sensor 162 may be part of a neuro-monitoring system 160 with a plurality of neuro-monitoring sensors 164.

In embodiments, the neuro-monitoring system 160 may be used to classify an item on the seating surface 16 in the seat assembly 12 as human or non-human. The neuro-monitoring sensor 162 may detect a band of frequencies and transmit the entire band of frequencies to the controller 104. The controller 104 may separate the entire band into various sub-bands by using filters to allow certain divisions. These sub-bands may overlap in frequency ranges. A general range of frequencies for each sub-band can be defined within a reasonable variance. A first sub-band can be up to four hertz. A second sub-band can be four hertz to seven hertz. A third sub-band can be seven hertz to fourteen hertz. A fourth sub-band can be fourteen hertz to about thirty hertz. A fifth sub-band can be about thirty hertz to about one hundred hertz. Other sub-bands may overlap these ranges, e.g., from eight hertz to thirteen hertz. A human occupant 40 will have neuroelectric activity in frequencies in at least the first, second, third, and fourth sub-bands. The neuro-monitoring sensor 162 may detect frequencies in the fifth band, but it is not required in order to classify the item.

With embodiments, a neuro-monitoring sensor 162 may detect a band of frequencies and transmit the band of frequencies along with characteristics of the strength of the frequencies to the controller 104 in a neuro-monitoring signal 166. The controller 104 may filter the neuro-monitoring signal and separate the frequencies into sub-bands for occupant classification. The controller 104 may use the strength characteristic 168 of the frequencies to triangulate the location of the head 42 of the occupant 40. For example and without limitation, if the head 44 of the occupant 40 is located directly in front of the neuro-monitoring sensor 162 in a XY plane, then the strength characteristic 168 of the band of frequencies will be strong (e.g. a smaller rate of decay). If the head 44 of the occupant 40 is located above or below the neuro-monitoring sensor 162 in a YZ plane, or located to the right or left of the neuro-monitoring sensor 162 in a XY plane, then the strength characteristic 168 of the band of frequencies will be weak (e.g. have a greater rate of decay).

Figure 10:
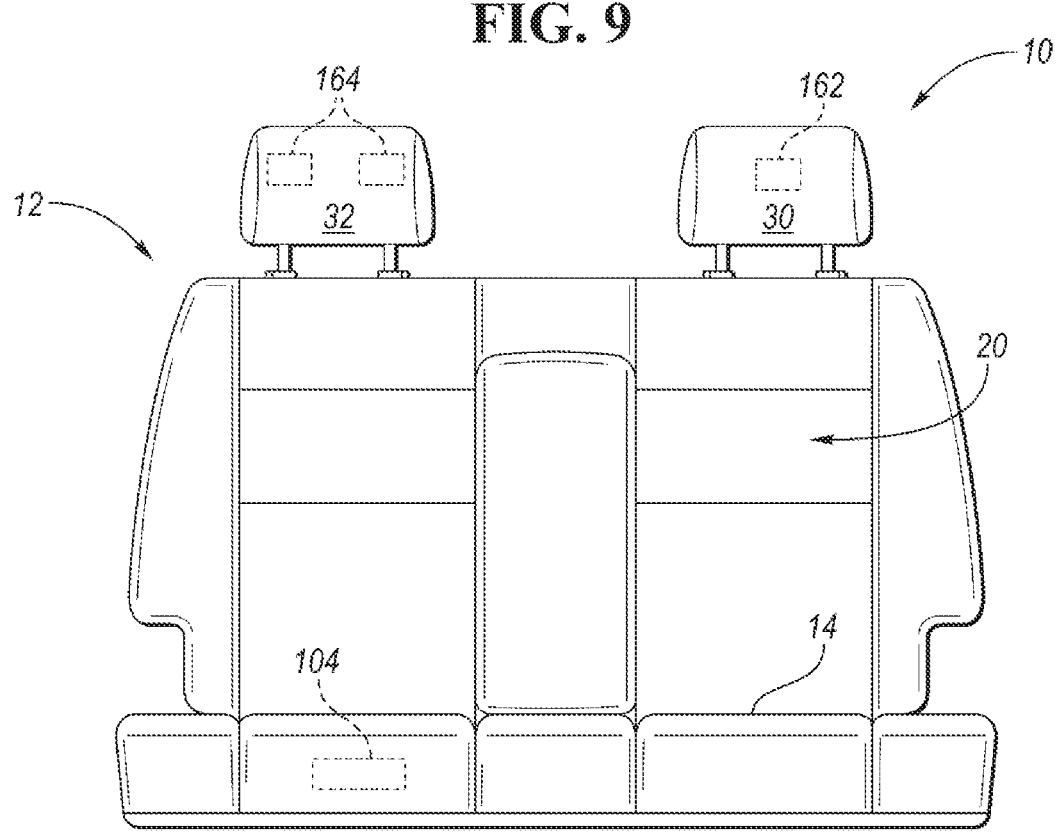
FIG. 10 is a front view of a seat assembly having an adjustable head restraint assembly according to one embodiment of the present disclosure.

In embodiments, the neuro-monitoring sensor 162 may have multiple antennas. The plurality of antennas may increase the accuracy of the approximate spatial location of the occupant 40 by receiving frequencies at each respective antenna. Each of the antennas may detect a band of frequencies. The strength of the frequency detected at each respective antenna may be indicative of the location of the occupant 40 relative to the respective antenna. For example and without limitation, the strength of the frequency 168 may be weaker (e.g. have a greater rate of decay) if the occupant 40 is farther from the neuro-monitoring sensor 162 whereas the strength of the frequency 168 may be stronger (e.g. have a smaller rate of decay) if the occupant 40 is closer towards the neuro-monitoring sensor 162. The neuro-monitoring sensor 162 may send a neuro-monitoring signal 166 to the controller 104 strength characteristics 168 for frequencies detected at each antenna. Referring to FIG. 10, the controller 104 may calculate a more accurate spatial location of the occupant using a plurality of neuro-monitoring sensors 164 where each neuro-monitoring sensor having multiple antennas, provides a neuro-monitoring signal 166 with strength characteristics 168 each respective antenna.

With embodiments, the controller 104 may use both the triangulated location of the heart 44 and the triangulated location of the lungs 46 to approximate the spatial location of the head 42 of the occupant 40 in the Y-direction. The controller 104 may send an adjustment signal 106 consisting of a predetermined distance, such as 8-16 inches, or 10-14 inches or 12 inches, to the head restraint adjustment assembly 36. The controller 104 may use the triangulated location of the head 42 and either the triangulated location of the heart 44 or the lungs 46 to better approximate the spatial location of the occupant 40. The controller 104 may send an adjustment signal 106 consisting of a predetermined distance, such as 1-6 inches, or 1-5 inches or 1-4 inches, to the head restraint adjustment assembly 36 in the X-direction.

With reference to FIG. 7, the transmitter 132 may emit a continuous wave of transmitting microwaves known frequency 136 and magnitude towards a seating surface 16. At step 202, the receiver 134 may receive a reflected energy wave 138, 138A, 138B, 138C and send a reflected energy wave signal 140 to the controller 104 a step 204. The controller 104 may filter the reflected energy wave signal 140 as described herein to create a filtered reflected energy wave 144 at step 206. The controller 104 determines at step 208 whether the occupant 40 is present or absent based on the filtered reflected energy wave 144, 144A, 144B, 144B as described herein. If the filtered reflected energy wave 144 does not include a reflected energy wave from respiratory activity 144B and/or a reflected energy wave from cardiac activity 144A or the decay rate is great, then an occupant is deemed absent and the controller 104 may send an adjustment signal 106 to the head restraint adjustment assembly 36 to move the head restraint assembly 30 to a non-use position (i.e. full down position 184 or stowed position 186, 187, 188) at step 210 and 212. The process may start all over again at step 202 such that the transmitter 132 may transmit microwaves of a known frequency 136 and magnitude towards a seating surface 16. If the filtered reflected energy wave 144 does include a reflected energy wave from respiratory activity 144B and/or a reflected energy wave from cardiac activity 144A and the decay rate is small, then an occupant is deemed present and the controller 104 may approximate the spatial location of the occupant 40 at step 216. At step 218, the controller 104 may send an adjustment signal 106 to the head restraint adjustment assembly 36 to move the head restraint assembly 30 to an in-use position (i.e. full-up position 180, mid travel position 182, or full down 184 position). The controller 104 may return to step 202 and repeat the process during regular intervals.

With reference to FIG. 7, the neuro-monitoring sensor 162 may monitor for neuroelectric activity. At step 202, the neuro-monitoring sensor 162 may detect neuroelectric activity from an occupant 40 in the seat assembly 12. The neuro sensor 162 may send a neuro-monitoring signal 166 to the controller 104 at step 204. The controller 104 may filter the neuro-monitoring signal 166 and identify sub-bands at step 206. The controller 104 determines at step 208 whether an item is present or absent based the neuro-monitoring signal 166 and strength of frequency 168 as described herein. If an item is not present (e.g. no neuroelectric activity is detected) the controller 104 may send an adjustment signal 106 to the head restraint adjustment assembly 36 to move the head restraint assembly 30 to a non-use position (i.e. full down position 184 or stowed position 186, 187, 188) at step 210 and 212. The process may start all over again at step 202 such that the neuro-monitoring system 160 is continuously monitoring for neuroelectric activity. If an item is in the seat assembly 12, at optional step 214 the controller 104 may determine if the object displays characteristics of living human neuroelectric activity. If the item is not a match for such activity, then the controller 104 may send an adjustment signal 106 to the head restraint adjustment assembly 36 to move the head restraint assembly 30 to a non-use position (i.e. full down position 184 or stowed position 186, 187, 188) at step 210 and 212. The process may start all over again at step 202 such that the neuro-monitoring system 160 is continuously monitoring for neurological activity. If the item is a match for human neuroelectric activity, then the controller 104 may estimate the spatial location of the occupant 40 as described herein at step 216. At step 218, the controller 104 may send an adjustment signal 106 to the head restraint adjustment assembly 36 to move the head restraint assembly 30 to an in-use position (i.e. full-up position 180, mid travel position 182, or full down 184 position). The controller 104 may return to step 202 and repeat the process during regular intervals.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention. Various steps in the method may be omitted, added, rearranged into another order, or performed sequentially or simultaneously.

What is claimed is:

1. A seat assembly, comprising:
   a seat back;
   an adjustable head restraint assembly connected to the seat back; and
   a sensor located in the seat assembly, adapted to detect when an occupant is present in the seat assembly, and adjust the head restraint assembly based on a determined size and spatial location of the occupant, wherein the spatial location of the occupant is determined based on computing triangulated locations of at least two body organs of the occupant.

2. The seat assembly of claim 1, wherein the sensor is adapted to identify and measure a biometric signal.

3. The seat assembly of claim 2, wherein the biometric signal is at least one of a heart beat, a respiratory signal, and a neurological signal.

4. The seat assembly of claim 2, wherein the sensor is a radar sensor.

5. The seat assembly of claim 1, wherein the sensor is located in or on the head restraint assembly.

6. The seat assembly of claim 5, wherein the sensor is a non-contact neuro-monitoring sensor capable of detecting and measuring neuroelectric activity.

7. The seat assembly of claim 1, wherein the head restraint assembly is capable of moving towards a non-use position when no occupant is detected, and the head restraint assembly is capable of moving towards an in-use position when an occupant is detected.

8. The seat assembly of claim 1, wherein the body organs include brain of the occupant, heart of the occupant, and lungs of the occupant.

9. The seat assembly of claim 1, wherein signals from the sensor are filtered to compute triangulated location of at least two body organs of the occupant.

10. The seat assembly of claim 1, wherein the sensor comprises at least one transmitter and at least one receiver.

11. The seat assembly of claim 10, wherein the at least one transmitter transmits a wave of energy and the at least one receiver receives a reflected energy wave.

12. The seat assembly of claim 11, wherein the at least one receiver sends a reflected energy wave signal to a controller.

13. The seat assembly of claim 12, wherein the reflected energy wave signal comprises time and angle of arrival information.

14. A seat assembly, comprising:
a seat back;
a head restraint assembly, disposed on the seat back;
a head restraint adjustment assembly, connected to the head restraint assembly and configured to adjust the head restraint assembly;
a sensor attached to the seat assembly, configured to detect an occupant when present; and
a controller in communication with the sensor, configured to:
determine a size and a spatial location of the occupant when present, wherein the spatial location of the occupant is determined based on computing triangulated locations of at least two body organs of the occupant, and
send an adjustment signal to the head restraint adjustment assembly to move the head restraint assembly towards an in-use position when the occupant is present, and move the head restraint assembly towards a non-use position when the occupant is absent.

15. The seat assembly of 14, wherein the sensor is a radar sensor.

16. The seat assembly of claim 14, wherein the sensor is a non-contact neuro-monitoring sensor capable of detecting and measuring neuroelectric activity.

17. The seat assembly of claim 16, wherein the neuro-monitoring sensor is disposed on the head restraint assembly.

18. A method comprising:
detecting an occupant when present in the seat using a sensor;
determining a size and a spatial location of the occupant using the sensor, wherein the spatial location of the occupant is determined based on computing triangulated locations of at least two body organs of the occupant; and
adjusting a head restraint that is adjustably coupled to a seat back of a seat in response to the determined size and the determined spatial location.

19. The method of claim 18, wherein the sensor is one of a bladder system capable of measuring a pressure, a radar sensor, and a non-contact neuro-monitoring sensor capable of detecting and measuring neuroelectric activity.

20. The method of claim 19, wherein the non-contact neuro-monitoring sensor is disposed on the head restraint.

* * * * *